United States Patent [19]
Bailey

[11] Patent Number: 5,730,595
[45] Date of Patent: Mar. 24, 1998

[54] DISPOSABLE PROPHYLAXIS ANGLE

[75] Inventor: Ronald L. Bailey, Harvester, Mo.

[73] Assignee: Young Dental Manufacturing Company, Earth City, Mo.

[21] Appl. No.: 632,906

[22] Filed: Apr. 16, 1996

[51] Int. Cl.$^6$ .................................................. A61C 3/06
[52] U.S. Cl. .......................... 433/125; 433/126; 433/166
[58] Field of Search .................................. 433/125, 126, 433/166

[56] References Cited

U.S. PATENT DOCUMENTS

| | | | |
|---|---|---|---|
| Re. 34,997 | 7/1995 | Kraenzle | 433/126 |
| 656,124 | 8/1900 | Kinnison . | |
| 1,522,757 | 1/1925 | Thiedemann . | |
| 1,534,817 | 4/1925 | Thiedemann et al. . | |
| 1,644,465 | 10/1927 | Chott | 433/166 |
| 3,239,788 | 3/1966 | Norman et al. . | |
| 3,239,789 | 3/1966 | Shaheen . | |
| 3,277,418 | 10/1966 | Norman et al. . | |
| 4,182,041 | 1/1980 | Girard | 433/125 |
| 5,052,071 | 10/1991 | Halm | 15/167.1 |
| 5,054,154 | 10/1991 | Schiffer et al. | 15/167.1 |
| 5,120,220 | 6/1992 | Butler | 433/126 |
| 5,156,547 | 10/1992 | Bailey | 433/125 |
| 5,178,538 | 1/1993 | Eckert | 433/166 |
| 5,224,859 | 7/1993 | Kraenzle | 433/126 |
| 5,334,020 | 8/1994 | Eckert | 433/166 |
| 5,398,369 | 3/1995 | Heinzelman et al. | 15/167.1 |
| 5,423,679 | 6/1995 | Bailey | 433/125 |
| 5,507,644 | 4/1996 | Kivlighan, Jr. | 433/166 |

*Primary Examiner*—Cary E. O'Connor
*Attorney, Agent, or Firm*—Polster, Lieder, Woodruff & Lucchesi

[57] ABSTRACT

A dental prophylaxis angle includes a body having a sleeve, a neck, and a one piece hollow head formed at the end of the neck. A drive member, including a drive gear and shaft is received in the body. A driven member, including a driven gear and shaft, is received in the head so that the driven and drive gears mesh with each other. A cap is received and secured in the head and snappingly receives the driven member. The cap locks the driven member in the head of the angle. The driven member includes a platform spaced above the driven gear having a diameter equal to the diameter of the head to close the opened head. The platform and driven gear define a channel. The cap has a side wall, a part of which is flexible. A finger extends inwardly from the flexible portion of the cap wall and into the channel between the driven gear and platform to snappingly secure the driven member in the cap. The cap includes a projection which interacts with the head to lock the cap in the head. A method of assembling the angle is also disclosed.

47 Claims, 7 Drawing Sheets

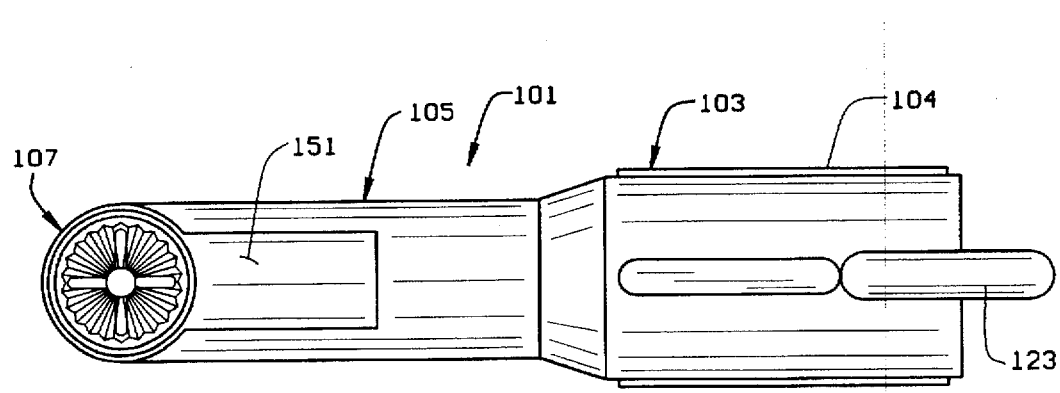
FIG. 13
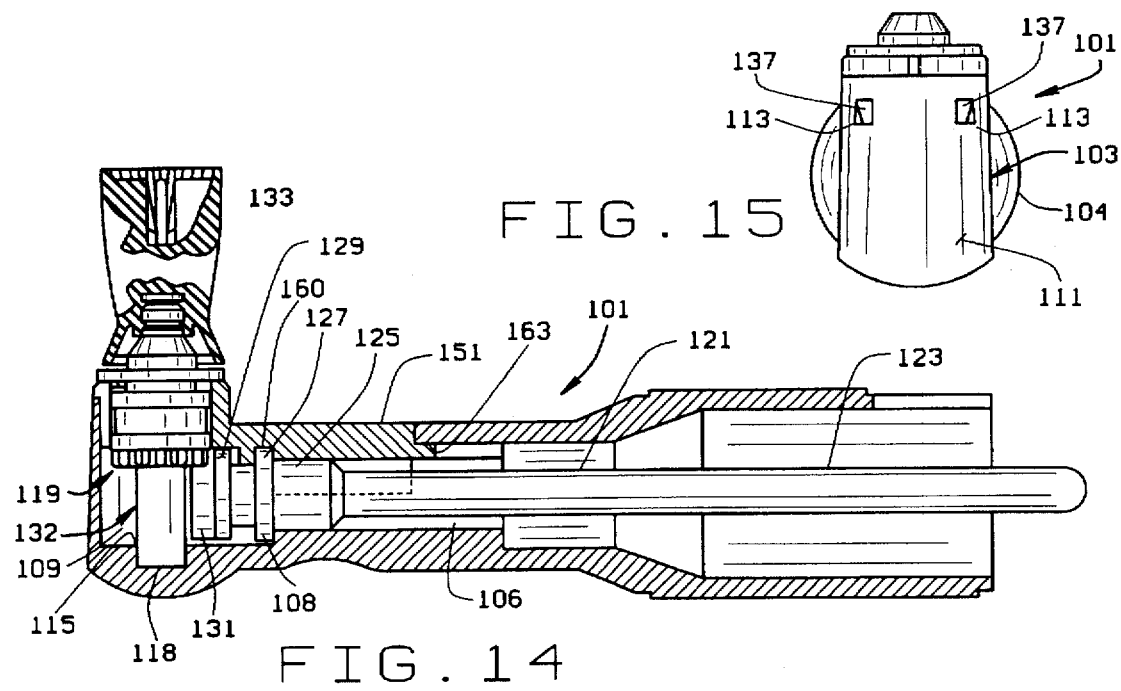
FIG. 15
FIG. 14
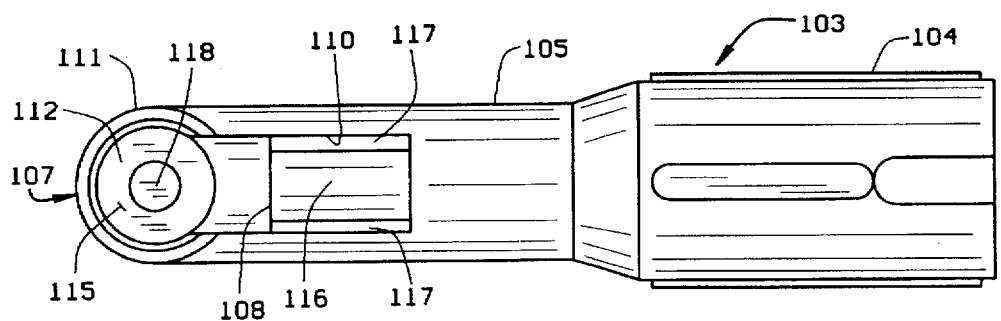
FIG. 16

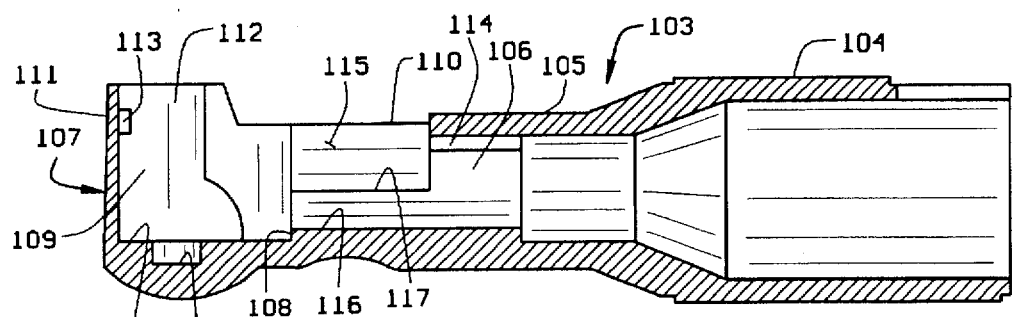
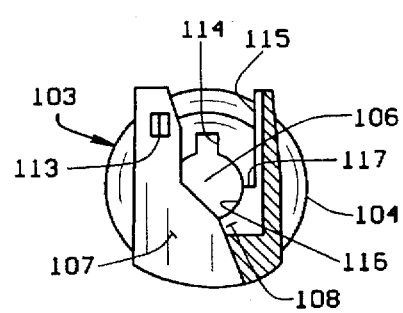
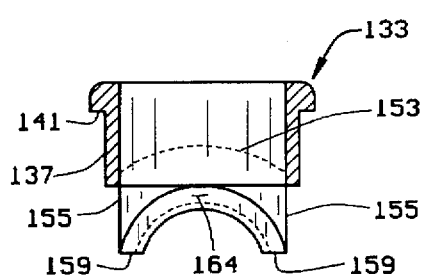
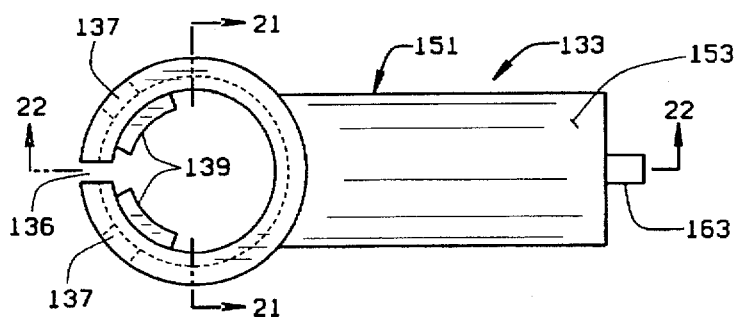
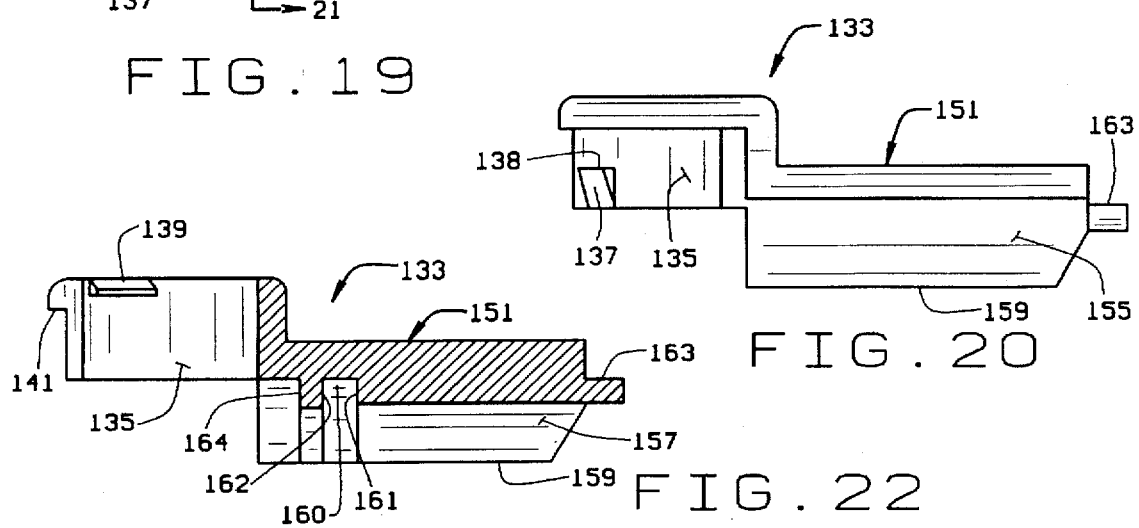

DISPOSABLE PROPHYLAXIS ANGLE

BACKGROUND OF THE APPLICATION

This invention relates to dental prophylaxis angles, and in particular to a disposable prophylaxis angle.

Dentists and hygienists use prophylaxis angles (prophy angles) to clean patients' teeth. As is known, a prophy cup is secured to the angle and is rotatably driven by a drive mechanism, typically a gear drive. The prophy cup is shaped to hold a desired amount of prophy paste which is used to clean a patient's teeth.

During use, the head of the angle is inserted in the patient's mouth, and thus comes in contact with bodily fluids, such as saliva and blood. If an angle is not sealed well, this saliva or blood can find its way into the angle. Thus, simply wiping down a metal angle with an alcohol rub between uses will not sufficiently clean or sterilize the angle. To properly sterilize metal prophy angles, the angles must be autoclaved. Further, every so often, metal angles must be disassembled and cleaned to remove any grit which may get into the angle. If the grit is not removed, the grit may interfere with the gearing, reducing the operating life of the metal angle. Metal angles must also be periodically lubricated to ensure that the gears run smoothly, quietly and efficiently to reduce heat build-up. As can be appreciated, metal prophy angles are care intensive.

Because metal angles are care intensive, plastic disposable prophy angles have become popular. Disposable angles are used once and thrown away. They do not need to be sterilized, cleaned, or lubricated by the dentist. A dentist can use thousands of disposable angles in a year. To make disposable angles attractive to a dentist to buy and use, the disposable angles must be made inexpensively. U.S. Pat. No. 5,156,547, which is incorporated herein by reference, and which assigned to the same assignee as the present application, discloses a disposable angle which utilizes a prophy cup which includes a screw. The prophy cup is threaded into a boss extending up from a driven gear of the angle. The use of the screw, which is made of brass, and the required step of screwing the cup onto the driven gear add expense and time to the construction and assembly of the angle. It would be desirable to eliminate the use of the screw to reduce component costs and manufacture and assembly time.

SUMMARY OF THE INVENTION

One object of the present invention is to provide a disposable prophy angle.

Another object is to provide such an angle which is easy to assemble.

Another object is to provide such an angle which may be produced inexpensively.

These and other objects will become apparent to those skilled in the art in light of the following disclosure and accompanying drawings.

In accordance with the invention, generally stated, a disposable prophylaxis (prophy) angle is provided. The prophy angle includes a body, a drive member, a driven member, a cap, and a dental tool. The angle's body has a hollow sleeve having an open back end, a neck formed at the front of the sleeve, and a hollow head formed at a front of the neck. The drive member is received in the body and includes a shaft which extends through the neck and sleeve of the body and a drive gear which is at least partially received in the head. The driven member is received in the head and includes a driven gear which meshes with the drive gear and a platform above the driven gear. The platform has a circumference approximately equal to the circumference of the head and serves to close the head. The cup extends upwardly from the driven member platform.

The cap is received in the head and receives the driven member to form an assembly which closes the opened head. The driven member is inserted into the cap from the top of the cap. The cap has a diameter slightly larger than the diameter of the driven gear and includes a wall having a top surface upon which the driven gear platform rests. A finger extends inwardly from the cap wall and interacts with the drive member to retain the driven member in the cap. The cap wall has a part thereof which may flex outwardly to allow the driven gear to pass over the finger. The cap wall is made to be expandable or flexible by forming a slit in the wall which extends downwardly from the top surface of the wall. In one embodiment, two spaced apart slits are formed in the cap wall to define a flexible arm, and it is the arm which will expand or flex radially. The finger is formed on the arm, preferably at the top of the arm. The flexible arm is flexed radially outwardly by the interaction of the driven gear and the finger when the driven member is inserted in the cap. The flexible arm and finger thus snappingly retain the driven member in the cap. The cap also has a lock which interacts with the angle body head to secure the cap in the body. In another embodiment of the cap, a single slit is formed in the cap and fingers are formed on either side of the slit.

The cap lock includes a projection formed on an outer surface of the cap wall. The body head includes a detent (and preferably an opening) formed in an inner surface of the head wall. The projection cooperates with the detent to lock the in the head of the angle body. In one embodiment, the area of the openings is substantially less than the area formed by the front of the head. The forward part of the head thus is substantially uninterrupted.

In another embodiment of the angle body, the neck of the body includes an elongate slot extending rearwardly from the body head. The neck includes side walls extending downwardly from side edges of the slot and an arcuate bottom surface exposed by the slot. The cap includes a rearwardly extending heel sized and shaped to be received in the slot in said neck. The heel includes side walls and an arcuate bottom surface. When the cap is inserted in the angle body, the heel bottom surface and the slot bottom surface define a circular being surface. The side walls of the neck and the heel are generally planar. The sleeve including steps which extend from the arcuate bottom surface to said side walls. The side walls of the heel are preferably sized to reach the steps. Thus, the bearing surface defined by the cap and sleeve bottom surfaces is substantially uninterrupted.

A semi-circular shoulder is formed in said neck and is exposed by the slot. The cap heel includes a semi-circular groove having a rear surface which is co-planar with the shoulder. The rear surface of the groove and the shoulder cooperate to form an annular surface against which a back surface of the gear abuts. The flange of the drive member is received in the groove to prevent axial movement of drive member in the body when the angle is assembled.

The sleeve includes a groove formed in an inner surface thereof and which extends rearwardly from the slot. The cap heel includes a rear finger which is received in the groove. The rear finger and groove cooperate to define a pivot point or locator for inserting the cap into the body. The groove formed in the neck also facilitates the insertion of the drive member into the body through the mouth of the head and the neck of the body. The drive member is inserted shaft first into the body by sliding the shaft into the mouth of the head and into the bore of the neck and sleeve. The shaft is flexed in this step. The shaft is inserted in this manner until the drive gear falls into the head. The drive member is slid rearwardly until the back of the drive gear abuts the shoulder of the neck. The cap, with the driven gear inserted therein, is then applied to the body to close the body.

To reduce assembly time of the prophy angle, the driven member and dental tool can be co-molded to define a unitary, one-piece component in which the driven assembly and dental tool are mechanically secured together. The dental tool and driven member are fused together along an interface between the driven member and dental tool. To increase the surface area of the interface, the driven member may include fins which extend upwardly from the platform, and the dental tool is then formed about the fins.

BRIEF DESCRIPTION OF THE DRAWINGS

FIG. 13 is a top plan view of an alternative embodiment of the angle, with a dental tool applied thereto, which allows loading of the drive through the top of the angle and which uses an alternative embodiment of the cap;

FIG. 14 is a cross-sectional view of the angle of FIG. 13

FIG. 15 is a front elevational view of the angle without the dental tool;

FIG. 16 is a top plan view of a body of the angle body;

FIG. 17 is a cross-sectional view of the body;

FIG. 18 is a front elevational view of the body, partly cut away;

FIG. 19 is a top plan view of a cap used with the body of FIG. 13;

FIG. 20 is a side elevational view of the cap;

FIG. 21 is a cross-sectional view of the cap taken along line 21—21 of FIG. 19; and FIG. 22 is cross-sectional view of the cap taken along line 22—22 of FIG. 19.

DESCRIPTION OF THE PREFERRED EMBODIMENT

Figure 1:
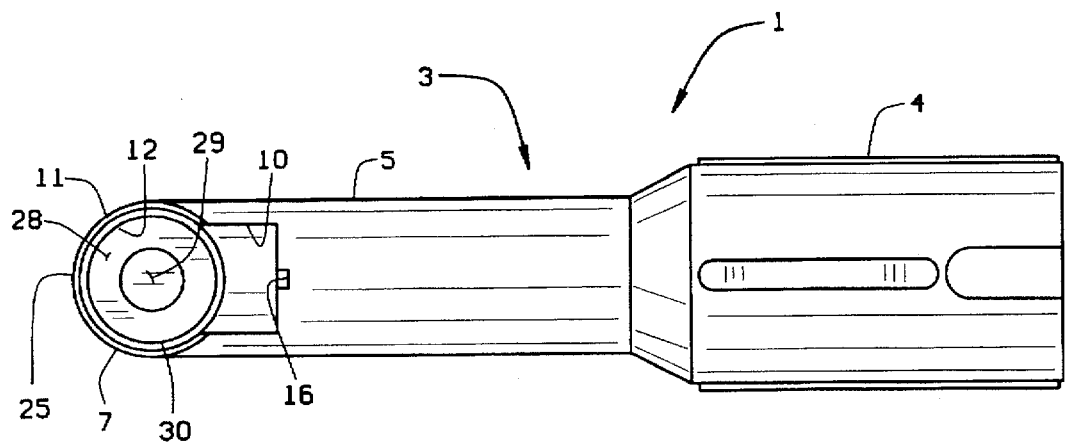
FIG. 1 is a top plan view of a body of an angle of the present invention.

A dental prophylaxis angle 1 of the present invention is shown generally in FIGS. 1–4. The angle includes a body 3 having a hollow sleeve 4 which is opened at a rear end to fit over the nose of a handpiece, such as a Doriot type handpiece, as is known. A hollow neck 5 extends forwardly of the sleeve 4. The sleeve 4 and neck 5 together define a bore 6. A one-piece head 7 is formed at the end of the neck. The body is preferably formed in accordance with the body described in U.S. Pat. No. 5,156,547, which is incorporated herein by reference, and includes an opening 9 formed in a forward portion of the head and which is axially aligned with the bore 6. The hollow head 7 includes an upper surface 11 which defines an upwardly opening mouth 12. A rectangular opening 10 is formed in the neck 5 behind the head 7 and opens into the head mouth 12. The upper surface 11 of the head thus does not define a complete circle. Rather the surface 11 completes an arc of about 270°. A notch 16 is formed at the back of the rectangular opening 10.

A drive member 14 is received in the bore 6 of the sleeve 4 and neck 5. The drive member is preferably a unitary, one-piece member including a shaft 13 which extends through the neck and sleeve to be received by the handpiece. A bearing surface 15 is formed at a forward end of the shaft 13; a shoulder or flange 17 is formed at a forward end of the bearing surface 15; and a gear 19 is spaced forwardly of the shoulder 17. The bearing surface 15 has a diameter larger than that of shaft 13 and slightly smaller than the inner diameter of the neck 5. The bearing surface 15 serves to maintain the drive member 14 substantially centered in the body bore 6 during use. The shaft 13 could be made wider in the neck area 5 of the body 3. However, the use of the reduced diameter shaft 13 in the neck 5 serves to reduce the amount of friction produced during operation of the angle. The gear 19 and shoulder 17 define a channel 21 therebetween. The gear 19 extends at least partly into the head 7. A shoulder 23 is formed near the forward end of neck 5. The flange 17 has a diameter greater than that of bore 6 and the flange 17 thus butts up against shoulder 23. The flange 17 thus facilitates positioning the drive member 14 in the body 3 and prevents the drive member 14 from passing too far through the body 3.

The head 7 includes an arcuate wall 25 defining an open area or open chamber 27 (FIG. 3) which is in communication with sleeve bore 6. The upper surface 11 is the upper surface of wall 25 and the mouth 12 provides access to the chamber 27. The head has a bottom or floor 28 having a bore or depression 29 formed generally in the center thereof and a groove 30 extending around at least a front portion of the floor 28. Groove 30 is generally concentrically formed with bore 29, and is shown in FIG. 1 to be circular.

A cup/cap assembly or closure assembly 31 (FIG. 4) is received in the open head 7 in area 27 to close the head and complete the angle 1. The cup/cap assembly 31 includes a cap 33 and a driven member 35. As can be appreciated, the head 7 forms only the head of the body 3 of the angle. When the body head 7 is closed with the cap 33, the body head 7 and cap 33 cooperate to form a head for the angle as a whole.

Figure 2:
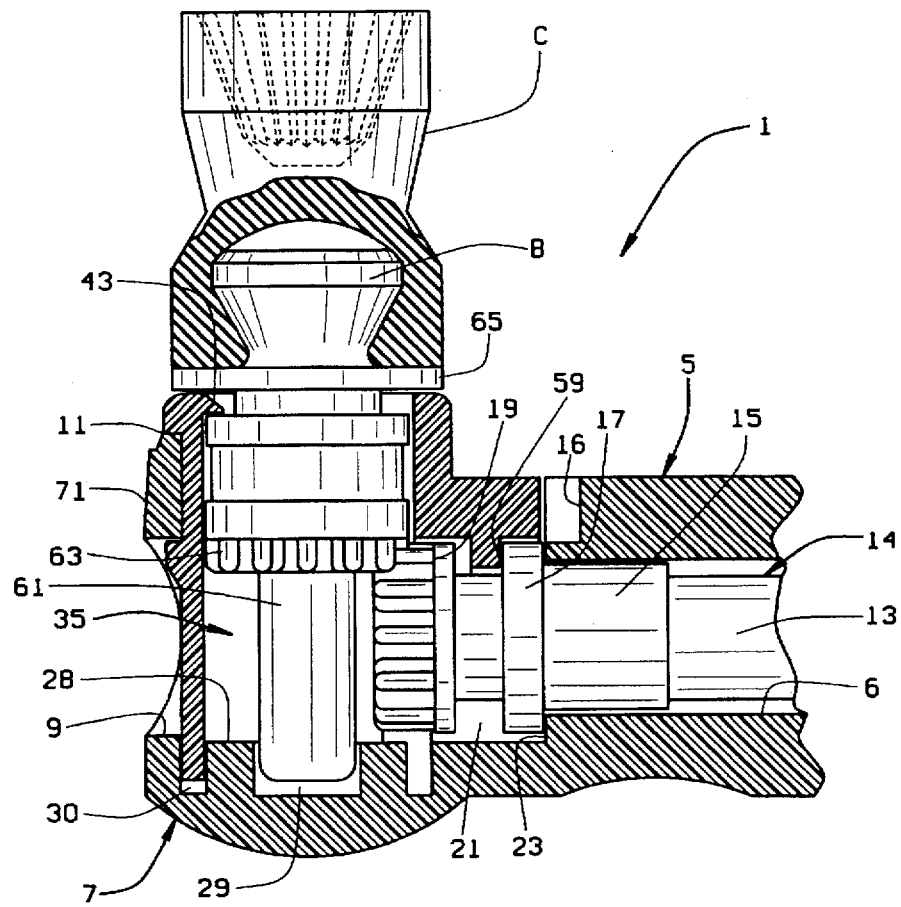
FIG. 2 is a cross-sectional view of an assembled dental prophylaxis angle of the present invention.
Figure 6:
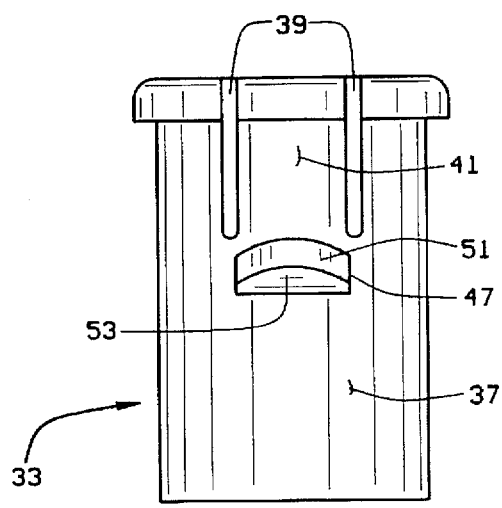
FIG. 6 is a front elevational view of the cap.
Figure 7:
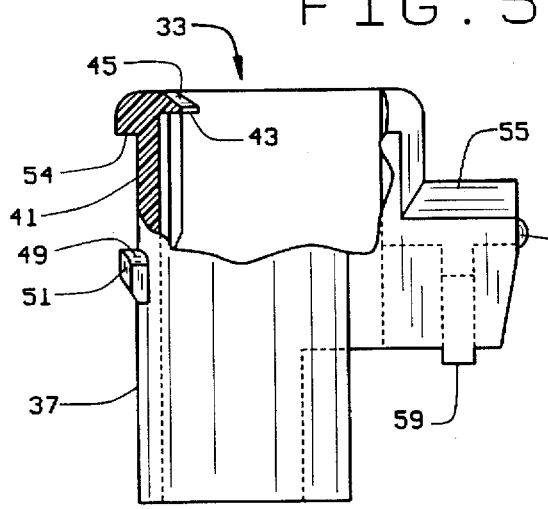
FIG. 7 is a side elevational view, partially cut away, of the cap.
Figure 8:
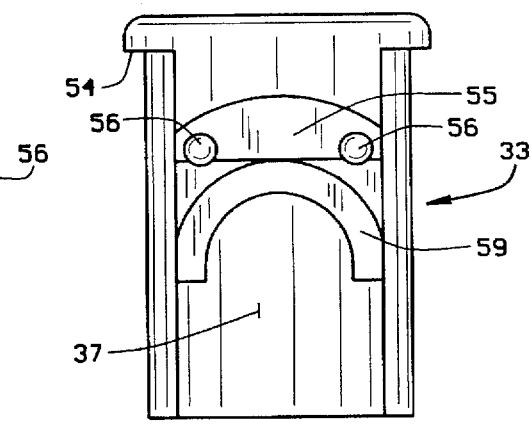
FIG. 8 is a rear elevational view of the cap.
Figure 9:
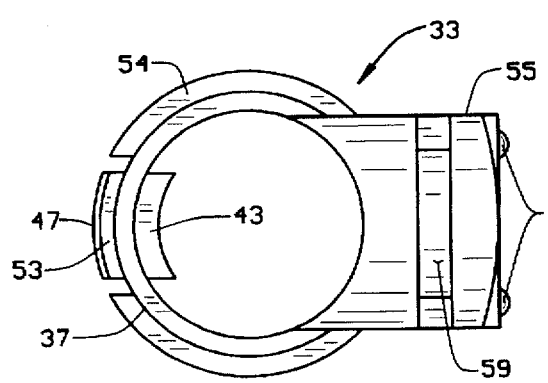
FIG. 9 is a bottom plan view of the cap.
Figure 10:
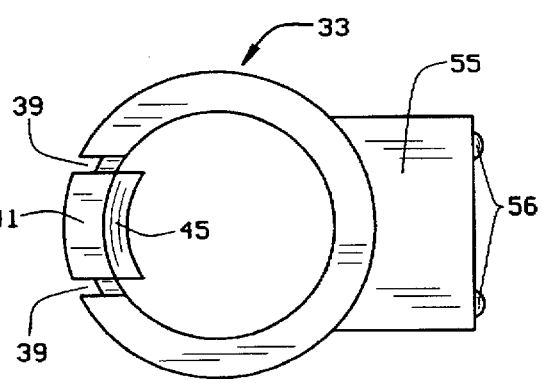
FIG. 10 is a top plan view of the cap.

The cap 33 (shown in detail in FIGS. 5–10) is received in the head 7. The cap forms or defines at the top thereof, an upwardly opening cylinder 36. The cap includes an arcuate front wall 37 which has a height generally equal to the depth of head 7. The wall 37 is shaped complementary to the inner surface of the head wall 25 to be received within the head 7. The cap wall 37, as seen in FIG. 2, is received in the groove 30 formed in the floor 28 of the head and closes the opening 9 formed at the front of the head. A pair of spaced apart slits 39 (FIG. 6) extend downwardly from the top of the cap 33 to define an arm 41. The slits are spaced apart a distance sufficient to allow arm 41 to be able to flex slightly in a radial direction. A finger 43 extends inwardly from the top of the arm 41 (FIGS. 7 and 9). The finger 43 preferably has a beveled top surface 45 and a generally horizontal bottom surface. A protrusion 47 is formed on the outer surface of the wall 37 beneath the arm 41. The protrusion 47 has a top surface 49 which is planar in cross-section and arcuate in front elevation. The surface 49 is shaped to conform generally to the shape of opening 9. The protrusion further has a generally flat front surface 51 and a beveled lower surface 53. The protrusion 47 has a width about equal to the width of the arm 41 and a depth slightly smaller then the width of the wall 25 of the head 7. A flange 54 extends around a majority of the cap 33 (as seen in FIGS. 8 and 9) at the top of the cap. The flange 54 and protrusion 47 are formed to have generally the same width (i.e. the extend radially outwardly from wall 37 an equal distance). As seen in FIG. 2, the flange 54 rests on the upper surface 11 of head 7. The protrusion 47 is positioned on wall 37 a distance below the flange 37 approximately equal to the distance between the top of the head opening 9 and the top 11 of the head so that the protrusion 47 (FIG. 2) will be received in the opening 9 when the angle 1 is assembled.

A heel 55 extends rearwardly from the cap 33. As described in the above noted patent, heel 55 covers the rectangular opening 10 in the neck 5 behind the head 7. The heel 55 includes a downwardly extending lip 59 which is received in the channel 21 of the drive member 14 to prevent axial movement of the drive member when the prophy angle 1 is assembled. Thus, the interaction of the flange 17 with the sleeve shoulder 23 and the heel lip 59 substantially prevents axial movement of the drive member in the completed dental prophy angle 1.

A pair of buttons 56 are formed on the back surface 58 of the heel 55. The is a small clearance between the back surface 58 of the heel 55 when the cap is inserted into the body 3 of the prophy angle 1. The buttons 56 are provided to fill this clearance to prevent the cap 55 from moving relative to the body sleeve 5 when the angle 1 is in use. When the cap is inserted in the body sleeve 5, the buttons 56 engage the back surface 60 (FIG. 3) of the sleeve opening 10, and are compressed by the engagement of the surfaces 58 and 60. The buttons 56 make a small groove in the sleeve opening surface 60 when the cap is inserted in the angle body 3. The buttons, as can be appreciated, create a tight fit between the cap 33 and body 3 and thus prevent movement of the cap relative to the body.

The driven member 35 is received in cap 33. It includes a shaft 61 which extends into the bore 29 in the head floor 28 when the angle 1 is assembled. A driven gear 63 is formed at or near the top of the shaft 61, and a platform 65 is spaced above the top of the gear 63. The platform 65 and gear 63 are separated by a stem 68 to define a channel 67. The driven gear 63 includes a gear body 64 having upper and lower bearing surfaces 66. The teeth of the gear 63 extend axially downwardly from the bottom of the lower bearing surface, the top of the upper bearing surface forms the top of the gear 63. The shaft 61 is sized so that the driven gear 63 will mesh with the drive gear 19 when the angle is assembled. The bearing surfaces 66 have diameters slightly wider than that of the body 64 and slightly smaller than the inner diameter of the cap 33. The use of the bearing surfaces reduces the amount of friction produced by the gear during operation from the amount of friction that would be produced if the gear body were of a single diameter.

The channel 67, formed by the platform 65 and gear 63, has a radial depth slightly greater than the length of finger 43 and an axial depth slightly greater than the depth of finger 43. The platform 65 has a diameter approximately equal to the diameter of the cap flange 54 or the head mouth 12. The platform 65 thus closes the cylinder 36 of the cap 33. The driven member 35 is preferably formed as a single piece, and thus the shaft 61, gear 63, and platform 65 are integrally formed, such as by injection molding. A prophylaxis cup C or other tool is secured to the driven member 35 above platform 65 such that the bottom-most surface of the cup is in contact with or slightly above the top of platform 65.

Figure 3:
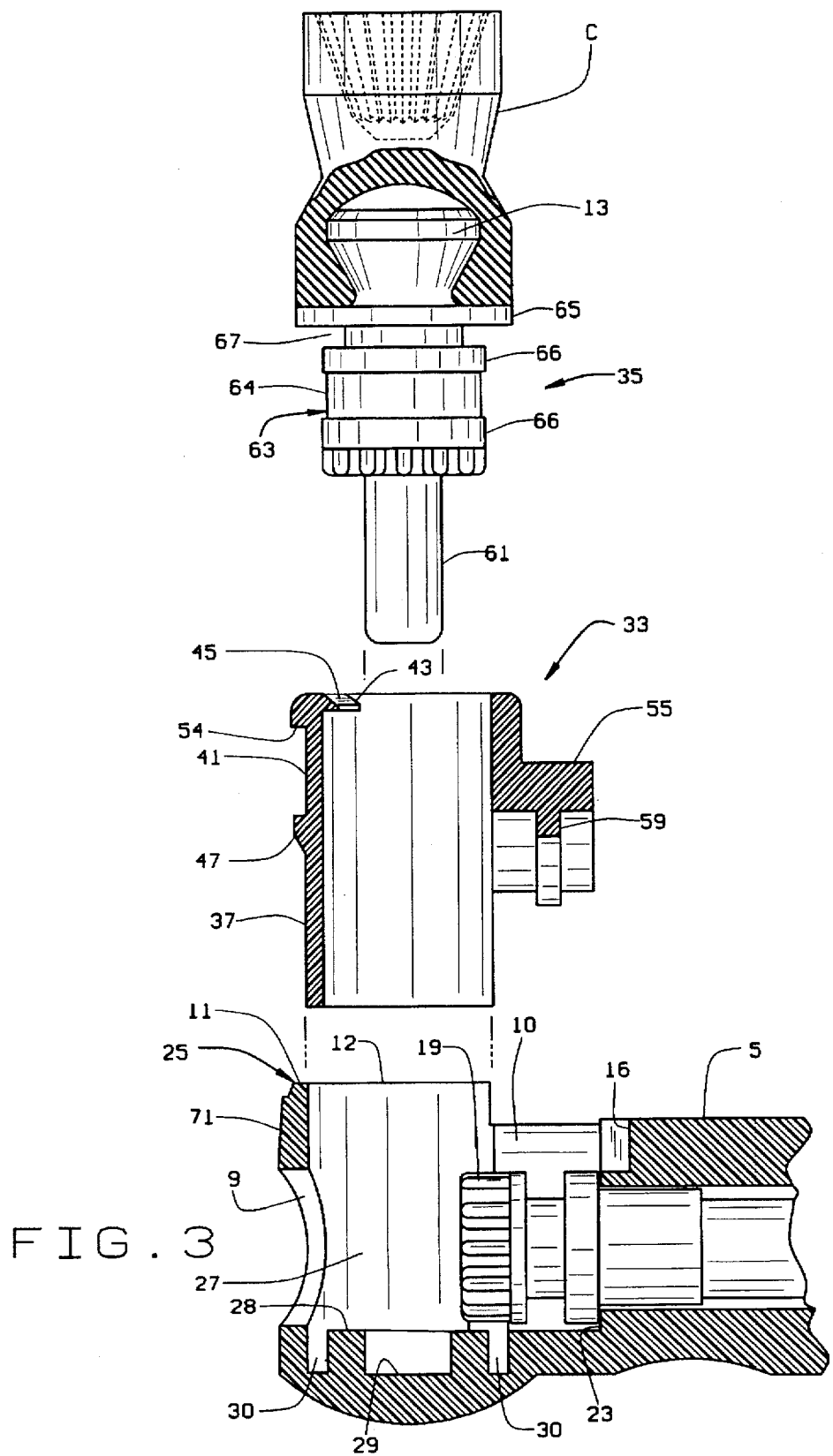
FIG. 3 is an exploded view of the angle, showing a driven member and cup, a cap, and a body of the angle.
Figure 4:
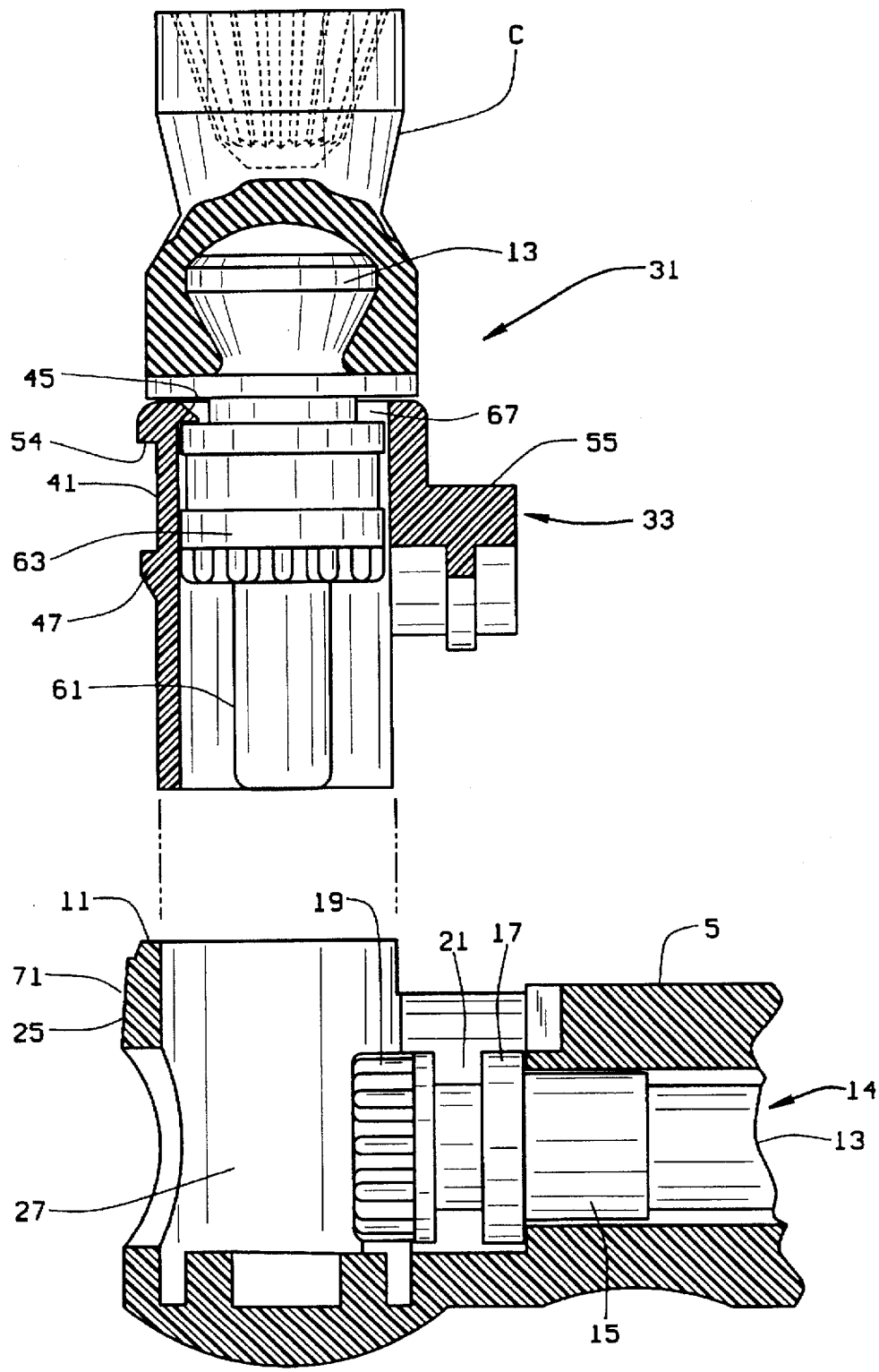
FIG. 4 is an exploded view of the angle showing a driven gear/cap assembly ready for insertion in a head of the angle body.
Figure 5:
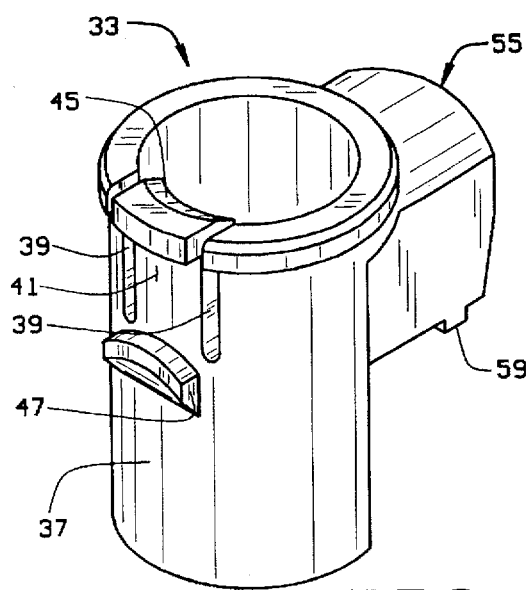
FIG. 5 is a perspective view of a cap of the present invention.
Figure 11:
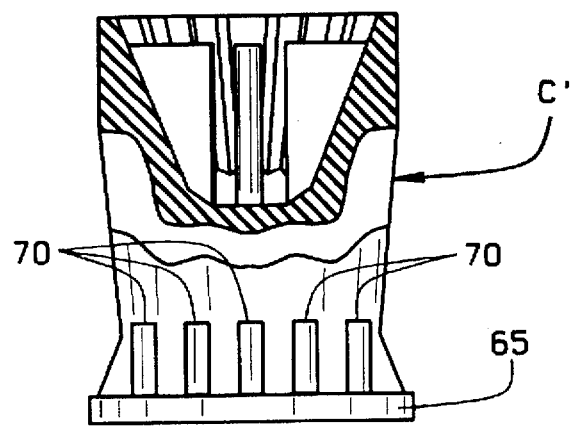
FIG. 11 is an elevational view, partly in cross-section, of a second method of securing the cup to the driven member.
Figure 12:
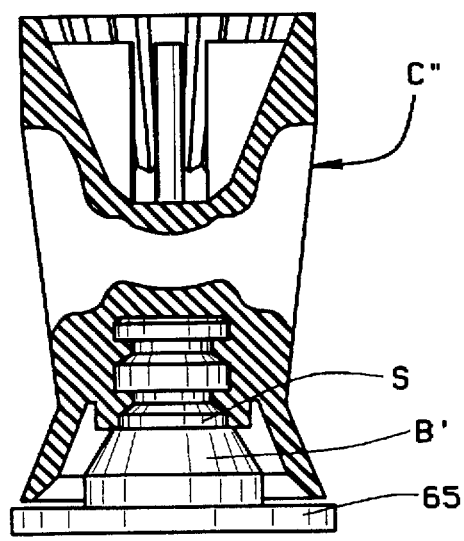
FIG. 12 is an elevational view, partly in cross-section, of a third method of securing the cup to the driven member.

The cup C may be secured to the member 35 in any desired manner. In FIGS. 2–4, the cup C is secured by means of a button B which is integrally formed with the driven member 35 and extends upwardly from the center of platform 65. The button B is received in an opening or hollow formed in the bottom of the cup. In FIG. 11, the cup C' is co-molded with the driven member to form a single one-piece driven member including the cup, platform, gear, and shaft. In FIG. 11, the platform 65 includes upwardly projecting teeth or fins 70 which form added surfaces to which the cup material can be co-molded. In FIG. 12, the cup C" is screwed onto the driven member 35. In this embodiment, the driven member 35 includes a plastic boss B' which extends upwardly from the platform 65. The boss B' is receives a screw S of cup C" which self-threads into the boss to secure the cup C" to the driven member 35. This embodiment allows for the switching of dental tools, if desired. For example, the cup C" may be replaced with a brush or another type of cup, etc.

Turning back to FIG. 11, the cup C' may be co-molded to the driven member in any manner desired. For example, the driven member may be molded first, and then placed in a mold in which the cup C' is formed. The cup C' can then be molded, for example, by compression or injection molding, on the driven member. The driven member may be only partially cured when the cup is molded thereon to enhance a mechanical bond between the cup and the driven member. This would of course be a two step process which would require two molds. Alternatively, the driven member and cup could be formed in one mold, but in two steps. The driven member would be formed initially, and at least partially cured, and then the cup would be molded on the driven member. A third possibility is to mold the driven member and cup simultaneously. This would use one mold and would be performed in a single step. The plastic from which the driven member is made would be placed into a bottom portion of the mold and the cup material would be placed into a top portion of the mold. This could be either by injection of the materials into the mold in an injection molding procedure. Alternatively, preforms could be used which are placed in the mold and then the driven member and the cup would be formed by compression molding. In either event, the driven member and cup would fuse together along an interface between the top of the platform 65 and the bottom of the cup.

If the cup and driven member are fused or bonded together along an interface, the fins 70 may not be needed. The mechanical or chemical bond formed in the molding procedure, no matter how performed, will be sufficient to hold the cup to the driven member during a prophylaxis procedure. The fins 70 may be added, as noted above, to provide more surface area for the interface. If the fins 70 are provided, openings could be formed in the fins through which the cup material flows during the molding of the cup. This would create a mechanical bond to hold the cup to the driven member, in addition to the fused interface between the cup and driven member.

To assemble the angle 1, the driven member 35 is inserted in the cap 33 from the top, as shown in FIGS. 3 and 4. When the driven member 35 is inserted into the cap, the gear 63 will interact with the beveled edge 45 of the finger 43 urging the arm 41 radially outwardly. When the gear 63 passes over finger 43, the arm 41 will snap back, urging the finger 43 into channel 67, as shown in FIG. 4. The finger 43 will thus interact with the channel 67 to prevent axial movement of the driven member 35 with respect to the cap. The driven member thus cannot be moved axially unless the finger 43 is moved out of channel 67. The cap/cup assembly is then inserted into the head 7 of the body 3 and locked in place. (FIG. 2) The cup itself may be attached to the cap/cup assembly at any time.

When the cap 33 is inserted into the head 7, the protrusion 47 will cause the portion 71 of the head wall 25 between the opening 9 and the upper surface 11 to deflect outwardly slightly. When the protrusion reaches the opening 9, the wall portion 71 will deflect or snap back into the space between the protrusion 47 and the cap flange 54. The protrusion 47 will thus create an interference fit between the head 7 and the cap 33 to prevent the cap from easily being removed without the use of tools. The complementary shapes of the protrusion 47 and the opening 9 form an even stronger interference fit which cannot be overcome merely by pulling on the cap. The wall portion 71 will prevent the arm 41 from being flexed. Thus, the finger 43 cannot be moved out of the channel 67 and the driven member is securely locked in the head. This is so, even though the finger 43 has a width much less than the circumference of the channel 67 of the drive member 35. When the cap 33 is inserted into the head 7, the heel 55 is received in the rectangular opening 10. The lip 59 is positioned on the heel to be received in the channel 21 of the drive member 14. The interaction of the lip 59 with the channel 21 will prevent the drive member 14 from moving axially relative to the angle body 3 and will thus hold the gears 19 and 63 in their meshing relationship while preventing the gears from being urged together too much to the point where the angle will not operate. The cap thus operates to lock the gears in the angle 1 when the cap is locked in the angle body.

Prior to inserting the closure assembly 31 in the head, the drive member 14 must be inserted in the angle. As set forth in the above noted patent, the drive member 14 is passed through the opening 9, shaft first, into the bore 6. When the cap 33 with the driven member 35 is inserted into the head, the driven gear will mesh with the drive gear, and the interaction of the cap with the body head will lock the drive and driven assemblies 14 and 35 in place in the body.

As can be seen, the angle 1 of the present invention is one which can be assembled quickly and easily. Because the screw has been omitted from the embodiments of FIGS. 1–4 and 11, the parts cost for producing the angle is reduced. Further, because the screw is not used in the embodiments of FIGS. 2–4 or 11, there is no screwing step involved in assembling the angle, reducing the time needed to put the angle together. The assembly time would be shortest in the embodiment of FIG. 11 in which the cup is co-molded to the driven member 35. Assembly here requires only two steps.

An alternate embodiment of the angle is shown in FIGS. 13–22. The angle 101 is shown generally in FIGS. 13–15. The angle 101 includes a body 103 having a hollow sleeve 104 which is open at its rear end to fit over the nose of a drive, as is known. A hollow neck 105 extends forwardly of the sleeve. An upwardly opening head 107 is formed at the end of the sleeve 105. The sleeve 104 and neck 105 define a bore 106 which expands from the transition between the neck and the sleeve. Thus, the bore 106 has a larger diameter in the sleeve 104 than in the neck 105. A shoulder 108 is formed in the bore 106 near the front of the neck 105. As seen in FIG. 18, the bore 106 in the neck 105 has a rectangular groove 114 formed in the top of the bore 106, which gives the bore a key-hole appearance. The groove 114 extends rearwardly from the shoulder 108 about ½ the length of the neck 105. The sleeve 105 also includes a semi-circular bearing surface 116. An elongate rectangular opening 110 is formed in the top surface of the body neck 105 and extends rearwardly from the head 107 approximately ½ to ⅓ the length of the sleeve. The opening 110 is defined by generally straight side walls 115. A generally flat surface or step 117 extends between the top edge of the bearing surface 116 and the side wall 115 of the opening 110.

The head 107 forms a chamber 109 defined by a generally circular wall 111 and has an upwardly opening mouth 112. The head 107 does not include an aperture equivalent to the aperture 9 in head 7 of angle body 3. Rather, the head 107 has two small spaced apart openings 113 (FIG. 15) generally on the from of the head. The openings 113 are substantially smaller in area than the front portion of the wall 111 of the head. The openings 113 have a height equal to about 10% to about 15% of the height of the outer surface of the head wall 111 and define an arc of only about 20°. The head wall 111 therefore is substantially uninterrupted. The two openings 113 are preferably spaced apart by about 90° of arc. The chamber 109 has a floor 115 and a bore 118 formed in the center of the floor.

The head 107 is closed by a cup/cap assembly 119 after a drive 121 is inserted in the neck and sleeve to extend out the back of the sleeve. The drive 121 includes a drive shaft 123, a beating 125, a pair of spaced apart flanges 127 and 129, and a drive gear 131. As noted above, the head 107 does not include an aperture in its front, and because the flange 127 is larger than the opening to the bore 106 defined by the shoulder 108, the drive 121 cannot be inserted from the rear of the angle. Rather, the drive is inserted into the top of the angle body through the mouth 112 in the head and the opening 110 in the neck. The drive 121 is similar to the drive 13 of FIG. 2. However, the drive 121 is preferably the drive shown and described in U.S. Pat. No. 5,531,599, which is incorporated herein by reference. As disclosed in that application, the structure of the shaft enables the shaft 123 to be highly flexible. The drive 121 is inserted by sliding the shaft 123 of the drive 121 into the bore 106 through the head mouth 112 and the neck opening 110. Because the shaft 123 will be angled relative to the bore 106, the end of the shaft will contact the bottom of the bore 106 in the neck 105. Because the shaft is highly flexible, the shaft will bend, without snapping or incurring undue strain, as it is inserted into the bore. The drive is pushed through the bore, until the gear 131 of the drive 121 falls into the head. The drive is then urged rearwardly until the flange 127 abuts the shoulder 108 of the neck 105. The groove 114 in the bore 106 in the neck 105 is sized to accommodate the drive shaft 123 as it is inserted in the bore 106. By providing the groove 114, the bending incurred by the shaft is reduced, and size of the opening 110 in the neck can be reduced.

The cup/cap assembly 119 includes a driven member 132 and a cap 133. The driven member is substantially identical to the driven member 33 of angle 1, and will not be further described herein. The cap 133 (shown more clearly in FIGS. 19–22), however, differs from the cap 33 of angle 1. The cap 133 includes a generally circular wall 135 having a slit 136 at the forward end of the cap. The slit is sized to allow the wall 135 to contract and expand slightly. Two fingers 137, having inwardly sloping bottom surfaces, are formed on the outer surface of the wall 135 and are sized and positioned to be snappingly received in the openings 113 in the wall 111 of the body head 107. The fingers or projections 137 have upper flat surfaces 138 which, when the angle 101 is assembled, interact with the openings 113 of the body head 107 to prevent the cap 133 from being removed from the head. The cap 133 also includes two inwardly projecting triangular fingers 139 which interact with the driven member 131, in the same fashion as the finger 45 of cap 33, to secure the driven member in the cap. Fingers 139 are preferably triangular in vertical cross-section and have a sloped upper surface and a generally horizontal bottom surface. A flange 141 extends radially outwardly from the top of the wall 135, and, when the angle 101 is assembled, the flange 141 rests on top of the wall 111 of the body head 107. The cap wall 135 has an outer diameter slightly smaller than the inner diameter of the wall 111 of the body head 107, and the flange 141 has an overall diameter approximately equal to the outer diameter of the head wall 111.

A heel 151 extends rearwardly from the back of the cap wall 135. The heel 151 includes an arcuate outer surface 153 which conforms to the shape of the body neck 105 and is positioned below the level of the cap flange 141. The heel 151 has generally straight side walls 155, an arcuate inner surface 157, and generally flat bottom surfaces 159. A semi-circular groove 160 having a back surface 161 and a front surface 162 is formed near the forward end of the heel 151 to receive the flange 127 of the drive member 121 to prevent axial movement of the drive member once the angle 101 is assembled. The surface 162 forms the rear surface of a finger 164 which extends inwardly from the inner surface of the heel. The bottom surface of the finger 164 is preferably slightly below the inner surface 157. Finger 164 is received in the groove formed in the drive member 121. The cap 151 also includes a finger 163 which projects rearwardly from the back of the heel and which is sized and positioned to be received in the groove 114 of the bore 106.

To assemble the angle 101, the drive member 121 is inserted in the sleeve as described above. The driven member 132 is inserted in the cap 133 to form the cup/cap assembly 119, as described above with respect to the angle 1. The cup/cap assembly 119 is then inserted into the body 103 to close up the body.

The cup/cap assembly 119 is inserted into the body 103 by inserting the heel finger 163 into the bore groove 114. The heel finger and groove then act as a pivot point, and the cap 133 is pivoted downwardly into place. As the fingers 137 pass over the inner surface of the wall 111 of the body head 107, the head 107 will expand slightly, as explained above. When the fingers come into alignment with the openings 113 in the head wall 111, the head wall 111 will spring back to its normal position, and the cap/cup assembly 119 will be locked in the head 107 of the body 103. When the cap 133 is inserted in the body, the wall 155 of the heel 151 will pass along the wall 115 of the cutout 110, and the heel surface 159 will rest on the surface 117 of the neck bearing 116. The neck bearing 116, which is semi-circular, and the inner surface 157 of the heel 151, cooperate to form a circular surface which defines the full bearing surface for the bearing 125 of the drive member 121.

The back surface 161 of the groove 160 in the cap heel 151 is aligned or coplanar with the front of the shoulder 108 of the angle body 103 when the cap 133 is inserted into the body 103. The shoulder 108 and the surface 161 thus define an annular surface which the flange 127 of the drive member 121 butts against. During operation, this surface bears the axial forces which are passed rearwardly through the angle. It thus forms an axial thrust bearing for the angle. The front surface 162 of the groove 160 prevents the drive member 121 from moving forwardly in the angle body 103. The groove 160 thus interacts with the driven member flange 127 to prevent substantial axial movement of the drive member 121 either forwardly or rearwardly. The shaft of the driven member 132 is received in the bore 117 in the floor 115 of the head chamber 109. The driven member shaft is sized so that the bore bears the downward forces applied to the angle during use. This prevents the drive gear 131 from becoming a load bearing member. If the gear 131 would be a load bearing member then the driven and drive gears could bind, and operation of the angle would be severely hindered.

As can be appreciated, the structure of either embodiment provides a dental prophy angle which can accept either screw type dental tools such as the cup of FIG. 12, button type cups, such as the cup of FIG. 3, or a co-molded cup/driven gear assembly, such as in FIG. 11. The interaction of the inner cap finger 43 or 139 with the groove 67 of the driven member 35 and the interaction of the outer cap finger 47 or 137, with the head openings 9 or 113 will securely hold the driven member in the angle such that it cannot be removed by simple pulling of the cup/driven member assembly. To remove the cup/cap assembly from the body head, the portion of the head wall above the outer cap finger 47 or 137 will have to be pulled outwardly or the finger 47 or 137 will have to be pushed inwardly a distance sufficient that the top surface of the finger will not be engaged by any portion of the opening. The forces applied during a prophylaxis procedure are not sufficient to move the finger of cap wall this distance. Thus, the angle of the present invention is one which is easy to assemble, yet which cannot be easily taken apart.

As variations within the scope of the appended claims may be apparent to those skilled in the art, the foregoing description is set forth only for illustrative purposes and is not meant to be limiting. The holes 9 and 113 could be replaced with dimples, or other depression shaped complimentary to the protrusions or projections 47 and 137, respectively. The body could be formed without the rectangular opening. The cap would then be formed without the heel and the upper surface of the head wall would form a complete circle. Although the gears are preferably made of plastics, they could be made of metal. The cap similarly could also be made of metal. The cap is shown to have one or two narrow slits. The cap could alternately be made with more slits or a single wide slot or opening. All that is necessary is that a slot or opening be provided which will allow the cap wall expand so that the upper bearing surface 66 of the drive member 35 can pass over the finger(s) on the inner surface of the cap wall and that the wall of the cap then snap back so that the finger(s) 45 engage the groove 64 in the gear body 63. The driven and drive gears can be made with any desired number of gear teeth. The choice in the number of gear teeth become a choice between tooth strength (fewer teeth) and smoothness of operation (more teeth). These examples are merely illustrative.

I claim:

1. A disposable prophylaxis angle comprising:
   a body including a hollow sleeve having an open back end; a hollow neck formed at the front of the sleeve; and a hollow head formed at a front of the neck;
   a drive member which is received in the body, said drive member including a shaft which extends through said neck and said sleeve and a gear which is at least partially received in said body head;
   a driven member which is received at least partially in the body head, said driven member including a driven gear which meshes with said drive gear and a platform above the driven gear, said platform having a circumference approximately equal to the circumference of said body head; and a tool extending upwardly from said driven member platform; and an upwardly opening cap which is received in said body head, said cap and body head cooperating to define a head of said angle; said cap receiving said driven member to form a sub-assembly which closes the body head; the driven member being inserted into said cap from a top of said cap; the cap including a wall having a top surface upon which the driven gear platform rests, an inner finger which extends inwardly from an inner surface of said cap wall and which interacts with said driven member to retain said driven member in said cap; said cap wall having at least a part thereof which flexes sufficiently to allow said driven gear to pass over said cap inner finger.

2. The disposable prophy angle of claim 1 wherein said wall of said cap includes a slit which extends downwardly from said cap wall top surface, said slit allowing said wall of said cap to flex.

3. The disposable prophy angle of claim 2 wherein said cap includes two inner fingers, one finger formed on each side of said slit, wherein said cap wall is flexed outwardly by the interaction of said driven gear and said inner fingers when said driven member is inserted in said cap, said fingers snappingly securing said driven member in said cap.

4. The disposable prophy angle of claim 2 wherein the cap wall includes two of said slits which extend downwardly from said cap wall top surface, said slits being spaced apart and defining a flexible arm; said flexing portion of said cap wall comprising said arm, said inner finger being formed on said flexible arm, wherein said flexible arm is flexed radially outwardly by the interaction of said driven gear and said inner finger when said driven member is inserted in said cap, said flexible arm and finger snappingly securing said driven member in said cap.

5. The disposable prophylaxis angle of claim 1 wherein said driven member platform is spaced above said driven gear to define a channel therebetween, said inner finger of said cap being received in said channel.

6. The disposable prophylaxis angle of claim 5 wherein said cap inner finger has a top surface, said finger top surface being beveled.

7. The disposable prophylaxis angle of claim 1 wherein said cap includes a projection formed on an outer surface of said cap wall, said head including a bore formed in an inner surface of said head wall, said projection cooperating with said bore to lock said cap in said head of said angle body.

8. The disposable prophylaxis angle of claim 7 wherein said bore extends through said head wall to define an opening in said head, said cap lock projection having a generally flat upper surface, said cap lock projection surface and said opening surface forming an interference fit to secure said cap in said head.

9. The disposable prophylaxis angle of claim 8 wherein said opening is substantially smaller in area than said head, said head including a front portion, said head front portion being substantially uninterrupted.

10. The disposable prophylaxis angle of claim 1 wherein said cap includes an outwardly extending flange, said flange being adjacent said cap top surface, said cap flange extending over a top surface of said body head.

11. The disposable prophylaxis angle of claim 1 wherein said tool defines a hollow lower area and said driven member includes a button extending upwardly from said platform, said button being received in said tool lower area to secure said tool to said driven member.

12. The disposable prophylaxis angle of claim 1 wherein said tool is a prophylaxis cup, said cup and driven member being co-molded.

13. The disposable prophylaxis angle of claim 1 wherein said body neck includes an elongate slot extending rearwardly from said body head, said neck including side walls extending downwardly from side edges of said slot and an arcuate bottom surface exposed by said slot; said cap including a rearwardly extending heel sized and shaped to be received in said slot in said neck, said heel including side walls and an arcuate bottom surface; wherein, when said cap is inserted in said angle body, said heel bottom surface and said slot bottom surface defining a circular bearing surface.

14. The disposable angle of claim 13 wherein said sleeve includes a groove formed in an inner surface thereof, said groove extending rearwardly from said slot, said cap heel including a rear finger which is received in said groove.

15. The disposable angle of claim 13 wherein said side walls of said slot are generally planar and the side walls of said heel are generally planar; said sleeve including steps which extends from said arcuate bottom surface to said side walls; wherein said side walls of said heel are sized to reach said step.

16. The disposable angle of claim 13 wherein a semi-circular shoulder is formed in said neck in said slot, said cap heel including semi-circular groove having a rear surface which is co-planar with said shoulder, said rear surface of said groove and said shoulder cooperating to form an annular surface against which a back surface of said gear abuts.

17. The disposable prophylaxis angle of claim 16 wherein said drive member includes a flange spaced from said drive gear, said flange being received in said groove to prevent axial movement of drive member in said body when said angle is assembled.

18. In combination a hollow cap and a driven member for a disposable prophylaxis angle, said angle including a body having an opened head; said cap being received in said head and said driven member being received at least partially in said cap, said cap and driven member defining a sub-assembly which closes said head of said body to define a head of said angle;

said driven member including a driven gear and a platform spaced above said driven gear, said driven gear and platform defining a channel therebetween;

said cap including a wall having an outer diameter slightly smaller than the diameter of said head of said angle body and an inner diameter slightly larger than the diameter of the driven gear, and an inwardly extending finger on said cap wall which extends into said channel of said driven member; at least a portion of said cap wall being flexible, said finger being formed on said flexible portion of said wall; said finger having a beveled upper surface such that said portion of said wall is flexed outwardly when said driven member is inserted in said cap, said finger snapping into said groove to snappingly hold said driven member in said cap.

19. The combination of claim 18 wherein said cap includes a slit extending downwardly from a top of said cap wall, said slit enabling said cap wall to flex.

20. The combination of claim 19 wherein said cap includes two of said fingers, said fingers being formed on opposite sides of said slit.

21. The combination of claim 18 wherein said cap includes two of said slits, said slits being spaced apart and extending downwardly from a top of said cap to define a flexible arm, said finger being formed on said arm.

22. The combination of claim 18 wherein said cap includes an outwardly extending flange, said flange resting on top of said head upper surface when said cap is inserted in said head.

23. The combination of claim 18 wherein the cap includes an outwardly extending projection on said cap wall spaced below said flange, said angle body head including an opening formed in an inner surface of said head, said head opening and said projection on said cap wall creating an interference fit to secure said cap in said head.

24. The combination of claim 23 wherein said projection is snappingly received in said head such that said cap cannot be easily removed from said head.

25. A method of assembling a disposable prophylaxis angle, the prophylaxis angle having a body including a hollow sleeve, a hollow neck formed at an end of the sleeve, and a hollow one-piece head at an end of the sleeve, the head defining an upwardly opening mouth; said method including:

inserting a drive member having a drive gear and a drive shaft into the body such that at least a portion of said drive gear is received in said hollow head;

inserting a driven member into a hollow cap and securing the driven member in the cap, the driven member including a driven gear, a platform spaced above the gear, the gear and platform defining a channel; said hollow cap including a wall which is in part flexible, a finger extending inwardly from said flexible portion of said cap wall, said finger interacting with said driven member channel to secure the driven member in the cap;

inserting and securing the cap in the head of the angle; said cap having a projection which is received in a depression formed on an inner surface of the head, the projection and depression interacting to lock the cap in the head.

26. The method of claim 25 wherein the step of inserting the driven member into the cap includes a step of deflecting said cap wall outwardly to allow said gear to pass by said finger of said drive member.

27. The method of claim 25 wherein the step of locking said driven member in the cap includes snappingly engaging said finger in said channel.

28. The method of claim 25 wherein said step of securing the cap in the head includes snappingly locking the cap in the head; the head having an opening and a wall above the opening; the cap projection being received in the opening, the cap projection deflecting the wall above the head opening as the cap is inserted in the head, the wall snappingly returning to place after said projection has passed said wall to snappingly lock the cap in the head.

29. The method of claim 25 including a step of securing a prophy cup to said driven member.

30. The method of claim 25 wherein the step of inserting the drive member into said body includes inserting said drive member, shaft first, into said body through the head of said body.

31. A prophy angle including:

a body having a sleeve, a neck, and a hollow head, said sleeve and said neck defining a bore which communicates with said head; said neck including an elongate slot formed therein which extends rearwardly from said body head, said sleeve including inner side walls which extend downwardly from said slot and an arcuate bottom surface exposed by said slot; said hollow head defining an upwardly opening mouth;

a drive member including a drive gear and a shaft, said shaft extending through said bore to be accessible from a rear of said angle;

a driven member received in said head and including a driven gear which meshes with said drive gear;

a cap which closes said upwardly opening head and slot, said cap including a rearwardly extending heel sized and shaped to be received in said slot of said sleeve, said heel having side walls which cooperate with said side walls of said sleeve and an arcuate surface which cooperates with said sleeve bottom surface to define a circular surface when said cap is placed on said angle body;

wherein said slot is sized such that said drive member can be inserted shaft first through said mouth of said head into said bore of said neck and said sleeve.

32. The prophy angle of claim 31 wherein said sleeve side walls are generally planar in said slot, said sleeve including a step extending from said side walls to said sleeve bottom surface; said heel having a flat bottom surface which rests on said step.

33. The prophy angle of claim 31 wherein a groove is formed in said bore, said groove extending rearwardly through at least a part of said neck from said slot of said neck.

34. The prophy angle of claim 33 wherein said heel includes a finger at an end thereof which is received in said slot.

35. The prophy angle of claim 31 wherein said slot extends at least one-half the length of said neck.

36. A method for assembling a prophylaxis angle, the angle including a body having a sleeve, a neck, a hollow body head defining an upwardly opening mouth; and an elongate slot extending rearwardly from said mouth, said sleeve and neck defining a bore which communicates with said body head; a cap which is received on said body to close said head and said slot; a one-piece unitary drive member including a shaft which extends through said bore and a drive gear which is received at least partly in said head; a driven member including a driven gear which meshes with said drive gear; and a dental tool received on said driven member; said method including:

inserting said drive member, shaft first, through said head mouth and into said body bore, said drive member shaft being sufficiently long to extend at least to the rear of said angle;

inserting said driven member into said head such that said driven gear meshes with said drive gear;

inserting said cap into said body to close said head mouth and slot; and securing said tool on said driven member.

37. The method of claim 36 wherein the method of inserting said drive member into said body includes flexing the shaft of said driven member a sufficient amount such that said driven member can be inserted into said body through said head mouth and slot.

38. The method of claim 36 wherein the steps of inserting said driven member and said cap into said head includes inserting said driven member into said cap to produce a sub-assembly and then inserting the sub-assembly into the head.

39. In combination, a driven member made of a first material for use in a prophylaxis angle and a dental tool made at least in part of a second material, the driven member including a platform, the dental tool being on the platform, wherein the driven member and dental tool are co-molded to define a unitary, one-piece component in which the driven member and dental tool are mechanically secured together; the driven member and dental tool being fused together along an interface between the driven member and dental tool.

40. The dental tool of claim 39 including fins extending upwardly from the platform, the dental tool being formed about the fins.

41. A disposable prophylaxis angle comprising:

a body including a hollow sleeve having an open back end; a hollow neck formed at the front of the sleeve; and a hollow head formed at a front of the neck;

a drive member which is received in the body, said drive member including a shaft which extends through said neck and said sleeve and a gear which is at least partially received in said body head;

a driven member which is received at least partially in the body head, said driven member including a driven gear which meshes with said drive gear and a driven gear shaft extending from a lower surface of said driven gear; and an upwardly opening cap which is received in said body head, said cap snappingly receiving said driven member; the driven member being inserted into said cap from a top of said cap.

42. The prophylaxis angle of claim 41 wherein said driven member includes an upper surface and a groove separating said driven gear from said driven member upper surface; the cap including a wall, a projection which extends inwardly from an inner surface of said cap wall and which interacts with said driven member groove to retain said driven member in said cap.

43. The disposable prophylaxis angle of claim 42 wherein said projection comprises at least one finger, said cap wall being sufficiently flexible to allow said driven gear of said driven member to pass over said finger.

44. The disposable prophylaxis angle of claim 43 wherein said cap includes at least one slit extending downwardly from an upper edge of said cap, said slit being sized to allow said cap wall to flex.

45. The disposable prophylaxis angle of claim 41 wherein said cap is snappingly received in said head of said angle body.

46. A disposable prophylaxis angle comprising:

a body including a hollow sleeve having an open back end; a hollow neck formed at the front of the sleeve; and a hollow head formed at a front of the neck;

a drive member which is received in the body, said drive member including a shaft which extends through said neck and said sleeve and a gear which is at least partially received in said body head;

a driven member which is received at least partially in the body head, said driven member including a driven gear which meshes with said drive gear and a driven gear shaft extending axially from a lower surface of said driven gear; and an upwardly opening cap which is received in said body head, said cap including at least a part which is moveable between a radially expanded position which permits axial passage of said driven member into the cap when said cap is away from said body head and a radially contracted position which retains said driven member in said cap, said body head maintaining said at least a part of said cap in said contracted position when said cap is received in said body head.

47. The prophylaxis angle of claim 46 wherein said driven member includes an upper surface and a groove separating said driven gear from said driven member upper surface; the cap including a projection which interacts with said driven member groove to retain said driven member in said cap.

* * * * *